(12) United States Patent
Campagna

(10) Patent No.: US 9,817,098 B2
(45) Date of Patent: Nov. 14, 2017

(54) SCALING OF LOCAL COILS OF A MAGNETIC RESONANCE IMAGING SCANNER

(71) Applicant: Swen Campagna, Engelthal (DE)

(72) Inventor: Swen Campagna, Engelthal (DE)

(73) Assignee: Siemens Aktiengesellschaft, München (DE)

(*) Notice: Subject to any disclaimer, the term of this patent is extended or adjusted under 35 U.S.C. 154(b) by 560 days.

(21) Appl. No.: 14/497,548

(22) Filed: Sep. 26, 2014

(65) Prior Publication Data
US 2015/0091574 A1    Apr. 2, 2015

(30) Foreign Application Priority Data
Sep. 27, 2013  (DE) .................. 10 2013 219 516

(51) Int. Cl.
| | | |
|---|---|---|
| *G01V 3/00* | (2006.01) | |
| *G01R 33/56* | (2006.01) | |
| *A61B 5/055* | (2006.01) | |
| *G01R 33/36* | (2006.01) | |

(52) U.S. Cl.
CPC .......... *G01R 33/5608* (2013.01); *A61B 5/055* (2013.01); *G01R 33/36* (2013.01); *G01R 33/3621* (2013.01)

(58) Field of Classification Search
CPC . G01R 33/5608; G01R 33/36; G01R 33/3621
USPC .......................................................... 324/318
See application file for complete search history.

(56) References Cited

U.S. PATENT DOCUMENTS

| | | | |
|---|---|---|---|
| 7,098,659 B2 | 8/2006 | Reykowski et al. | |
| 7,869,536 B2* | 1/2011 | Li | H04B 7/0413 |
| | | | 375/267 |
| 2009/0230966 A1* | 9/2009 | Ehnholm | G01R 33/3415 |
| | | | 324/322 |

FOREIGN PATENT DOCUMENTS

DE    10313004 B3    1/2005

OTHER PUBLICATIONS

German Office Action in corresponding German Patent Application No. DE 10 2013 219 516.8 dated May 15, 2014, with English translation.

* cited by examiner

*Primary Examiner* — Susan Lee
(74) *Attorney, Agent, or Firm* — Lempia Summerfield Katz LLC

(57) ABSTRACT

A scaling unit (1) for reception antennae (A1, A2, A3, A4) of a plurality of local coils (LS) of a magnetic resonance imaging scanner (MRT) includes a plurality of signal inputs (in1, in2, in3, in4) configured for the reception of signals from the reception antennae (A1, A2, A3, A4), and a plurality of signal outputs (out1, out2, out3, out4) configured for the output of unaltered and/or altered signals from the reception antennae (A1, A2, A3, A4).

20 Claims, 2 Drawing Sheets

SCALING OF LOCAL COILS OF A MAGNETIC RESONANCE IMAGING SCANNER

RELATED APPLICATIONS

This application claims the benefit of German Patent Application No. DE 102013219516.8, filed Sep. 27, 2013. The entire contents of the priority document are hereby incorporated herein by reference.

TECHNICAL FIELD

The present teachings relate generally to a scaling unit for reception antennae of local coils of a magnetic resonance imaging scanner (MRT). The scaling unit has a plurality of signal inputs configured for the reception of signals from the reception antennae, and a plurality of signal outputs configured for the output of unaltered and/or altered signals from the reception antennae. In some embodiments, the present teachings further relates to a reception device, a local coil, a reception-and-transmission device having a corresponding scaling unit, a magnetic resonance imaging scanner, and a method for signal transmission.

BACKGROUND

In order to produce MRT images having an optimum signal-to-noise ratio (SNR), reception antennae may be placed in close proximity to an object to be measured (e.g., a patient or subject). Such reception antennae are known as local coils. The local coils may be in the form of reception coils but may also be transmission coils.

A local coil is a physical unit that may be used by an MRT user. The physical unit may have a plurality of logical subunits (e.g., coil elements) that the user may individually select or deselect for a measurement. A coil element in turn may combine a plurality of reception antennae (e.g., local coil antennae) that produce the individual MRT signals that are ultimately used in the MRT imaging as single and independent signals. By way of example, a local coil may have three individually addressable coil elements. Each of the three individually addressable coil elements may have six individually addressable reception antennae. Thus, in this example, a local coil may have 18 single reception antennae.

A multiplicity of reception antennae may provide faster MRT measurements through parallel imaging methods. A higher antenna density of reception antennae (e.g., the number of reception antennae of the local coil) corresponds to higher image quality. However, the multifold reception antennae produce many independent signals that may be transmitted via numerous cables and digitized by many analog-to-digital (AD) converters.

A switching matrix may be used between the reception antennae and the AD converters to make at least one selection of signals, such that the number of AD converters is limited to an amount n (e.g., the maximum number of reception antennae that may be used at one time). The amount n is limited by the magnitude of the homogeneity volume of the MRT. In practice, not all of the coil elements may simultaneously come to be in the homogeneity volume of the MRT.

If, for reasons of cost, a system having fewer than n receivers (e.g., A/D converters plus infrastructure) of the image-processing unit is used, an unaltered set of local coils may not allow the entire homogeneity volume of the MRT to be used for imaging. There are an insufficient amount of receivers of the image-processing unit available for image processing. Conventional local coils are not compatible with a small number of receivers of an image-processing unit for image processing. As a result, the signals from the reception antennae may be customized in a scaling unit prior to transfer to the image-processing unit. In addition, a plurality of local coils may be used in an MRT. The plurality of local coils may all be connected to the scaling unit.

DE 10313004 B3 describes a combination network that allows a combination of single signals from a multiplicity of reception antennae. The combination network is provided with a multiplicity of inputs and an identical number of outputs. All the inputs are connected to all the outputs within the combination network. Within the combination network, the single signals from the multiplicity of reception antennae may be weighted and/or phase shifted.

The data signals from the local coils are redistributed by the combination network. The original data signals from the antennae are applied to the input, and the signals that are referred to as "modes" are applied to the output. With an appropriate design of the combination network, the signal at output 1 may provide a sum of all the antennae (e.g., "CP mode") and at least geometrically cover the reception range of these antennae (e.g., as a single larger virtual antenna). The additional signals from the higher modes may be mixed from the original signals, such that the additional signals add new information content to the respective previous modes. Thus, combinability of the local coil is achieved. The use of a single reception circuit allows signals from the entire geometric range to be used, and the use of further reception channels allows the use of further modes, thereby improving image quality and facilitating parallel imaging methods, for example.

The combination network described in DE 10313004 B3 is complex and expensive to design, manufacture, maintain and repair. In addition, individual tuning may be used during production.

Although the modes hold the same information content as the original signals when all of the modes are used and the combination network is correctly implemented, the signal characteristic is substantially altered. Moreover, the use of the higher modes in unaltered algorithms for MRT image calculation may be problematic.

SUMMARY AND DESCRIPTION

The scope of the present invention is defined solely by the appended claims, and is not affected to any degree by the statements within this summary.

If a plurality of signals is to be used as the sum signal from a local coil or coil element for raw data acquisition for an image calculation, the original signals (e.g., the unweighted and/or inphase original signals) may be used and may be less problematic with respect to unaltered signal characteristics.

The present embodiments may obviate one or more of the drawbacks or limitations in the related art. For example, in some embodiments, the circuit complexity for a scaling unit may be substantially reduced while a comparatively good or even improved SNR (and, therefore, a comparatively good or improved MRT image quality) is maintained.

It is to be understood that elements and features of the various representative embodiments described below may be combined in different ways to produce new embodiments that likewise fall within the scope of the present teachings.

In some embodiments, at least in a summed signal mode, all of the signal inputs are connected, for signaling purposes, to a common signal output. In some embodiments, the common signal output is a single signal output. The sum of the signals from all the signal inputs is applied to the signal output. In some embodiments, the signals are unaltered (e.g., unweighted and inphase) signals. The additional signal outputs for the plurality of signal outputs are each connected, for signaling purposes, to a single signal input that is individually associated with the respective signal output. The respective signal from the associated signal input is applied to these additional signal outputs. In some embodiments, the respective signal from the associated signal input is unaltered. As used herein, the phrase "connected for signaling purposes" indicates that the respective outputs and inputs are coupled to one another in such a way as to conduct signals or to conduct data. In some embodiments, the coupling is an electrically conductive coupling. In some embodiments, components may be arranged in between, (e.g., optocouplers, light guides, wireless transmission links, etc.). In some embodiments, the components may be configured to alter the signal. In some embodiments, a simple electrically conductive connection by a conductor track or the like may be used.

By forming the sum of all the single antenna signals in the scaling unit (e.g., the unaltered single antenna signals), by conducting the remaining single antenna signals (e.g., the unaltered remaining single antenna signals) through the scaling unit, and by transmitting these signals (e.g., via a multiplexing/demultiplexing apparatus), the circuit complexity is reduced without substantially impairing the image quality. The scaling unit in accordance with the present teachings may be used flexibly. Almost any desired local coil (including a plurality of local coils), and the coil elements and reception antennae of local coils, may be used for an MRT and the image-processing unit of an MRT without complex customizations.

An inexpensive scaling unit is provided since all of the input signals are applied in summed form to a single output of the scaling unit for transmission to an image-processing unit of the MRT. A multiplicity of signals from reception antennae of a local coil (e.g., head coil) are combined in the examination area of the patient and forwarded as a single summed signal value to the image-processing unit of the MRT. This local coil, like other local coils, may be segmented into different areas (e.g., front/back and top/bottom). Each of these segments may include a plurality of reception antennae. The summed signal may be ascertained from each of the segments in order to improve the image quality.

The "unweighted, inphase" summation is a simple and inexpensive variant for a summed signal. Since the complexity may be expended for a single output signal, other more involved interconnections may also be used.

For an ideal CP signal (e.g., a kind of sum of a plurality of antennae in the CP mode), a complex-weighted sum may be formed. For example, three different weighting factors, at least one of which may even be in complex-value form, may be used from three antennae. An advantage over a rigid redistribution matrix is that the original signals for raw data acquisition may be used for further image calculation.

The scaling unit in accordance with the present teachings may be used for reception antennae of at least one coil element of at least one local coil of an MRT. The at least one local coil may have a multiplicity of coil elements (e.g., three) that in turn reveal a multiplicity of reception antennae (e.g., six).

Thus, the scaling unit may have a multiplicity of signal inputs (e.g., 18) configured for receiving the signals from a multiplicity of reception antennae (e.g., 18), and also a multiplicity of signal outputs (e.g., 18) configured for outputting the unaltered and/or altered signals from the multiplicity of reception antennae.

In contrast to DE 10313004 B3, the signals from the reception antennae may be applied to the signal outputs of the scaling unit in unweighted and/or inphase form. In alternative embodiments, the signals from the reception antennae may likewise be applied to the signal outputs of the scaling unit in weighted and/or phase-shifted form.

An alternative scaling unit contains a switching element that may be used to change over, in an electrically conductive manner, the signal output at which the sum of the signals from all the signal inputs is applied in the summed signal mode to a signal input associated with the signal output in a single signal mode. Each of the signal inputs is connected, for signaling purposes, to a single associated signal output. The respective signal (e.g., unaltered signal) from the associated signal input is applied to the single associated signal output.

Alternatively, the switching element may be provided on the transmission side in order to transmit the output signals to the image-processing device.

In some embodiments, the switching element may be an electromechanical switch or a pushbutton switch. In other embodiments, the switching element may be an electronic switch in the form of a semiconductor switch (e.g., a semiconductor relay or transistor).

In some embodiments, in the single signal mode, there may be a single signal from a signal input applied to the signal output to which the sum of the signals from all the signal inputs is applied in the summed signal mode. Alternatively, there may not be a single signal from the signal input applied, in the single signal mode, to the signal output to which the sum of the signals from all the signal inputs is applied in the summed signal mode. The signal output is a separate summed signal output that is used exclusively for forwarding the summed signal from all the single signals to the image-processing unit of the MRT.

In some embodiments of a scaling unit, each of the signal inputs, for signaling purposes, is connected to a single associated signal output. The respective signal from the associated signal input (e.g., the unaltered signal) may be applied to the single associated signal output. The signals may be configured to be retrieved by an image-processing unit of the MRT in a single signal mode. All of the signal inputs and/or all of the signal outputs may be connected, for signaling purposes, to an additional common signal output. The sum of the signals from all the signal inputs may be applied to the additional common signal output. In some embodiments, the signals are unaltered (e.g., unweighted and inphase). The signal may be configured for retrieval by an image-processing unit of the MRT in a summed signal mode.

All of the inputs of the scaling unit may be connected to all of the outputs of the scaling unit and to an additional summed output of the scaling unit. In such embodiments, the above-described switching element may not be used.

In some embodiments, a reception device having a scaling unit in accordance with the present teachings is provided. The plurality of reception antennae of the local coils of an MRT may be individually connected, for signaling purposes, to the plurality of associated signal inputs of the scaling unit. In addition, the plurality of signal outputs of the scaling unit may be connected, for signaling purposes, to a plurality of associated signal inputs of an image-processing unit BV of the MRT.

In some embodiments, a local coil for a reception device having a scaling unit in accordance with the present teachings is provided. The local coil has a plurality of reception antennae and at least one scaling unit.

In some embodiments, a reception-and-transmission device having scaling units in accordance with the present teachings is provided. A plurality of scaling units may be present. The respective signal outputs of the scaling units, to which the sums of the signals from all the signal inputs are applied, are connected, for signaling purposes to a multiplexer. The multiplexer is connected via a transmission channel wherein signals or data are conducted (e.g., electrical conduction, optical conduction, wirelessly via an air interface by electromagnetic radio waves, etc.) to a demultiplexer. The demultiplexer may be used to individually supply the sums of the signals from all the signal inputs of each scaling unit to the image-processing unit of the MRT. In some embodiments, arbitrary multiplexing methods may be used (e.g., time-division multiplexing methods, frequency-division multiplexing methods, etc.).

In some embodiments, a number of signal outputs of each of the plurality of scaling units to which the signals from the signal inputs are applied may be connected, for signaling purposes, to a multiplexer. The multiplexer is connected via a transmission channel to a demultiplexer that may be used to individually supply the signals from the signal inputs of each scaling unit to an image-processing unit of the MRT.

The two above-described signal transmissions may be combined with one another via a multiplexer/demultiplexer. A first transmission channel of the transmission unit may be used to transmit the plurality of sums of the input signals in multiplexed form (e.g., by time-division multiplexing in serial succession or by frequency-division multiplexing) to the image-processing unit of the MRT. A second transmission channel of the transmission unit may be used to transmit the plurality of input signals themselves, (e.g., by time-division multiplexing in serial succession or by frequency-division multiplexing) to the image-processing unit of the MRT. Similarly, other multiplexing methods may be used. The combined signal transmissions via multiplexer/demultiplexer may be used for more complex scaling units.

In some embodiments, the multiplexer may be integrated directly into at least one of the scaling units and/or at least one of the local coils. For signaling purposes, this configuration provides simple electrically conductive coupling between the signal outputs of the summed signals and the signal outputs of the single signals. Only a single connecting cable may be used for coupling to the demultiplexer if the signal transmission is mechanically coupled via the transmission channel (e.g., via electrical and/or optical conductors). If the signal transmission via the transmission channel takes place using radio waves, the transmission device may be integrated directly into at least one of the scaling units and/or at least one of the local coils and/or the multiplexer.

In some embodiments, a magnetic resonance imaging scanner (MRT) is provided. The MRT has a reception-and-transmission unit and scaling units in accordance with the present teachings.

In some embodiments, a method for signal transmission in a scaling unit, a reception unit, a local coil, a reception-and-transmission unit, or an MRT is provided. At least in a summed signal mode, all of the signal inputs are connected, for signaling purposes, to a common signal output (e.g., a single common signal output). The sum of the signals from all the signal inputs is applied to the single common signal output. In some embodiments, the signals from all the signal inputs are unaltered (e.g., unweighted and inphase). Each of the additional signal outputs from the plurality of signal outputs may be connected, for signaling purposes, to a single signal input individually associated with the respective signal output. The respective signal from the associated signal input (e.g., unaltered signal) is applied to the additional signal outputs.

In some embodiments, the value of the signal from the reception antenna may be calculated at the signal input that is not directly connected to an associated signal output in the summed signal mode. The value of the signal from the reception antenna may be calculated from the absolute value of the difference between the sum of all the signals from the signal inputs that is applied to the associated signal output and the sum of all the remaining single signals that are applied to the remaining signal inputs or signal outputs. If the summed signal is a complex-weighted sum, the original signal may be reconstructed using the meta information that is stored for each individual coil (e.g., in the EEPROM of the coil itself). By way of example, the weighting factors may be stored as meta information.

DETAILED DESCRIPTION

Figure 1:
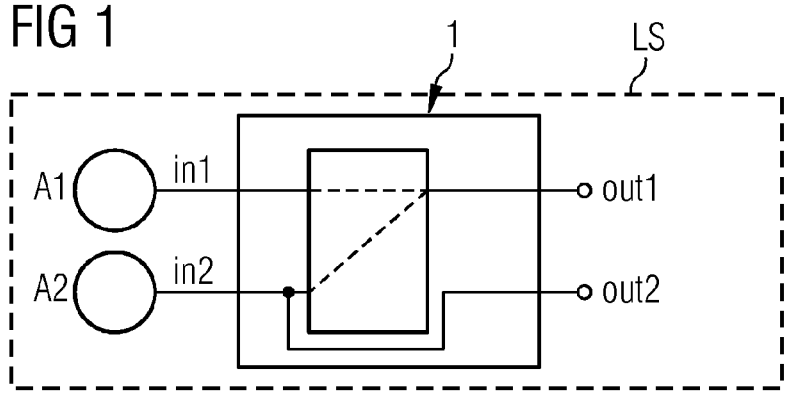
FIG. 1 shows a schematic illustration of an example of a local coil with a scaling unit having two inputs and two outputs.
Figure 2:
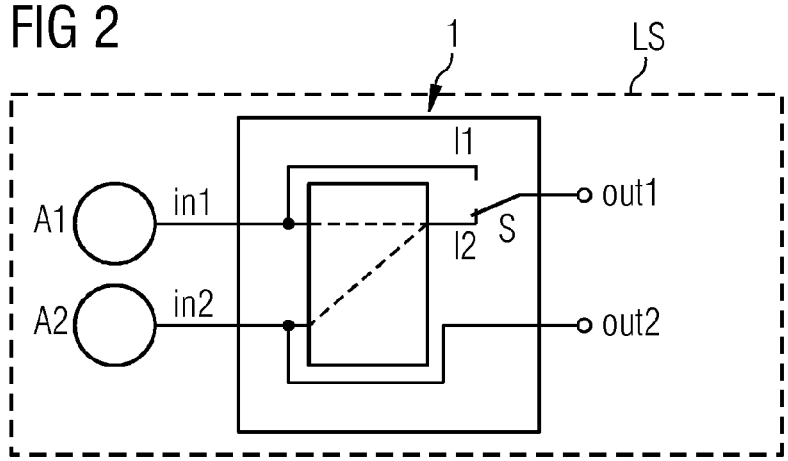
FIG. 2 shows a schematic illustration of an example of a local coil with a scaling unit as in FIG. 1 having a changeover switch for an input/output.
Figure 3:
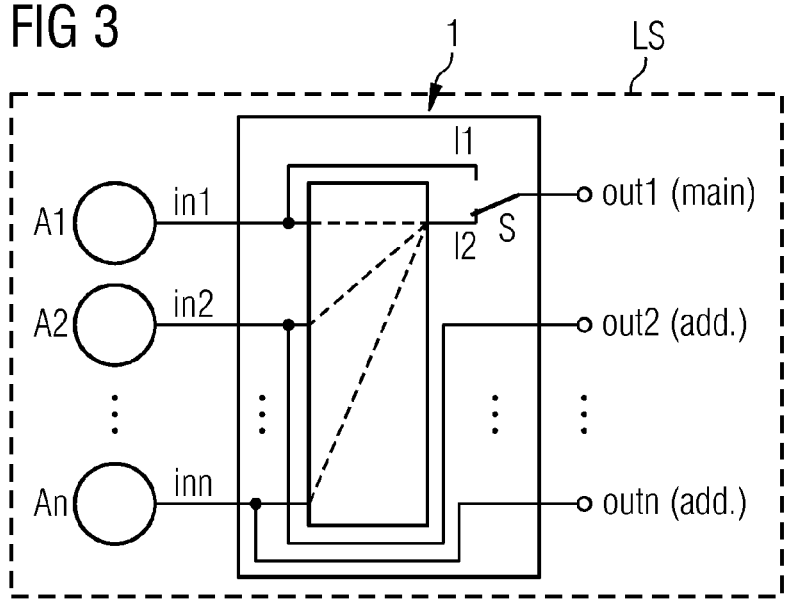
FIG. 3 shows a schematic illustration of an example of a local coil with a scaling unit having n inputs and n outputs and a changeover switch for an input/output.

Each of FIGS. 1 to 3 shows reception antennae A1, A2, A3, A4, ..., An (hereafter, "antennae") that are coupled to a scaling unit 1 in accordance with the present teachings. The antennae A1, A2, together with the scaling unit 1, may be part of a local coil LS. The local coil LS may have a multiplicity of additional standard components (not shown), such as preamplifiers, switch elements, and detuning devices for deactivating and activating the antennae A1, A2, A3, A4, ..., An.

FIG. 1 shows a simple configuration of a scaling unit 1 as part of a reception unit 2 (see FIG. 4) of one or more local coils LS. There are two individual reception antennae (A1, A2), two inputs (in1 and in2), and two outputs (out1 and out2). Similarly to FIG. 3, more than two inputs and two outputs may be provided. The number of inputs may differ from the number of outputs since the signals are combined within the scaling unit 1. The input signals may also be split. In some embodiments, the number of inputs and the number of outputs are identical.

In some embodiments, the scaling unit 1 in accordance with the present teachings includes two inputs (in1, in2) for the signals from the two antennae A1 and A2 and two outputs (out1 and out2) for the transformed data (e.g., signals). Signal combination of the signals of the two antennae A1 and A2 to form a summed signal may take place for a single summed signal (e.g., CP mode) that is made available at the output out1 to provide advantages of a combination network. The output out2 has the original antenna signal in2 applied to it with all the advantages of a local coil LS without a combination network. The internal signal combination (e.g., summation) is simpler than a conventional combination network with n inputs and n outputs, since only one output is combined (e.g., the simplest scenario for a summed signal from directly adjacent antennae).

The switch S shown in FIG. 2 is omitted from FIG. 1. The summed signal combined from all the inputs in1, in2 is applied to the output out1. If all the outputs out1, out2 are used in the MRT image calculation BV, all of the information content is likewise present albeit not in the original manner. Rather, the respective first signal at the output out1 has a different characteristic. However, suitable methods nevertheless allow image reconstruction by, for example, reconstructing the original signal during preprocessing from the summed signal and additional signals that are present. The procedure may then continue in a conventional manner.

In FIG. 2, the scaling unit 1 of FIG. 1 is provided switch S for input/output in1/out1.

The scaling unit 1 includes two inputs (in1, in2) for the signals from the two antennae (A1 and A2), and two outputs (out1 and out2) for the transformed data (e.g., signals). A signal combination to produce a summed signal may take place for a single summed signal that is available internally at the point I2. If just a single signal is requested by the scaling unit 1 for further processing in the MRT image processing BV, the switch S is put into the position I2. The summed signal (e.g., CP mode) is made available at the output out1 to provide advantages of a combination network. If, however, more than one signal is requested for further processing in the MRT image processing BV, the switch S is put into the position I1 and the original antenna signals are applied to the outputs out1 and out2 with all the advantages of a local coil LS without a combination network. In addition, the internal signal combination (e.g., summation) is simpler than a conventional combination network with n inputs and n outputs, since only one output out1 may be combined (e.g., the simplest scenario for a summed signal from immediately adjacent antennae A1, A2, . . . , An).

In some embodiments, there are more than two input signals, as shown in FIG. 3.

The scaling unit 1 may be used within a local coil LS, and may not correspond to the number of antennae A1, A2, . . . , An of a coil element. Thus, by way of example, a local coil LS may include three coil elements with six antennae (A1, A2, . . . , An) each. Three scaling units 1 per coil element may be equipped with six inputs/outputs (in1 to in6 and out1 to out6) via one scaling unit, with three inputs/outputs (in1 to in3 and out1 to out3) each via two scaling units 1, or with two inputs/outputs (in1, in2 and out1, out2) each via three scaling units.

Further simplification of the scaling unit 1 may further reduce the component complexity to a minimum.

Methods in accordance with the present teachings may also be applied to systems wherein the received signals are transmitted by a multiplexing unit MUX and demultiplexing unit DEMUX of a transmission unit 3. The multiplexing unit MUX and the demultiplexing unit DEMUX are connected to one another via a data transmission cable 4. Without scalability, the signals that go to a common multiplexer may be selected or deselected only together for the purpose of MRT image reconstruction BV. The reason is that the selection of the user or of the SW framework ultimately controls the wires and switching matrixes to be used. As a result, the signals that are multiplexed onto a physical medium are together.

Figure 4:
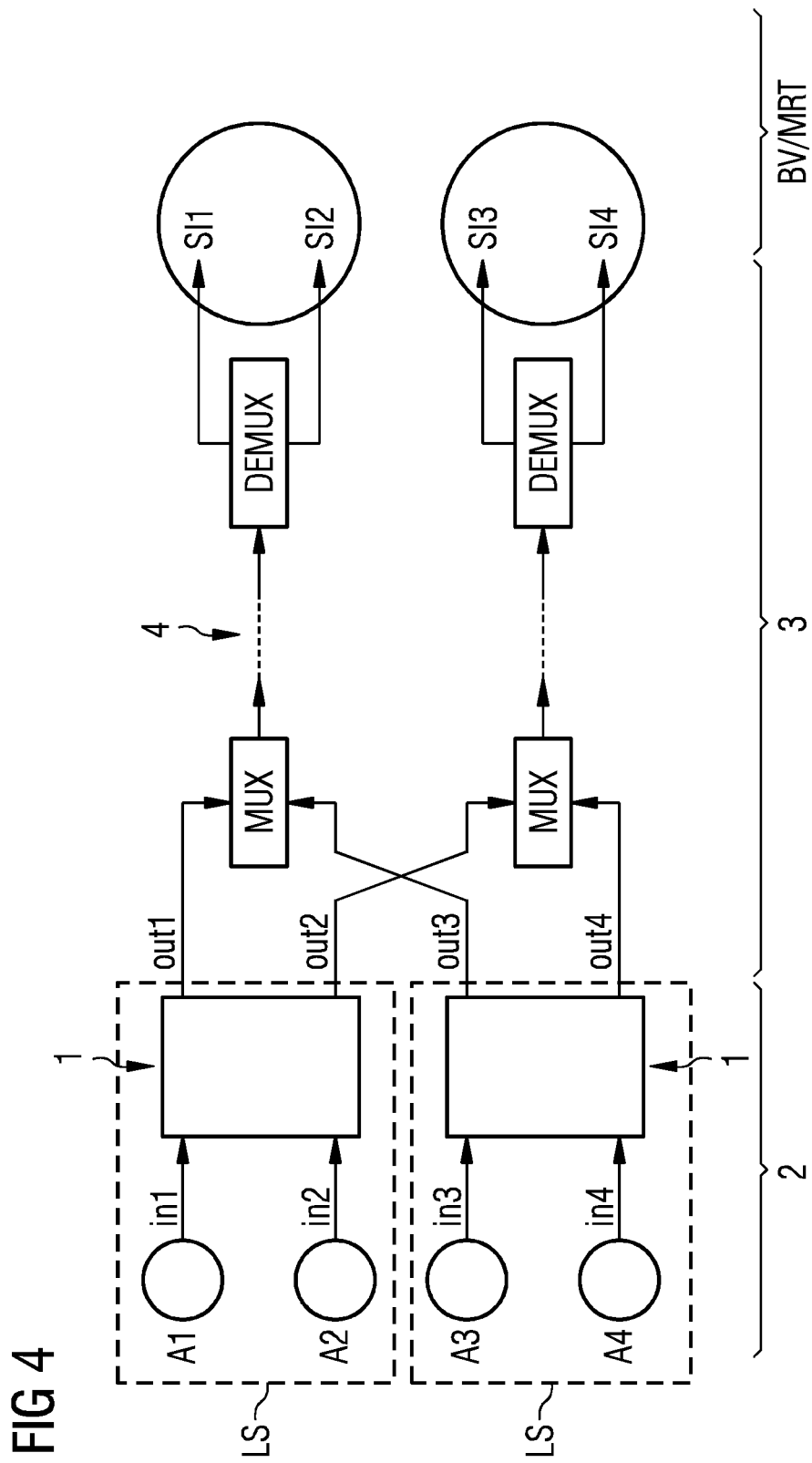
FIG. 4 shows a schematic illustration of a plurality of scaling units as in FIGS. 1 to 3, wherein the output signals from the scaling units are routed via a multiplexer/demultiplexer unit to an image-processing unit BV of a magnetic resonance imaging scanner MRT.

FIG. 4 shows two signal pairs. More general cases with more than two signal pairs (e.g., two or more of the scaling units 1 in FIGS. 1 to 3) may be used.

The signal paths that contain the combined signal may be multiplexed with one another instead of having one such signal path with just an optionally selected signal path. The main signal pair S11 and S12 transmitted to the MRT image processing BV on the upper transmission channel 4 in FIG. 4 corresponds to the signals combined from the antennae A1 and A2 or A3 and A4 (e.g., the signals at the outputs out1 and out3). The main signal pair may be formed by the respective sums of the respective inputs in1+in2 and in3+in4 if the signal pair S13 and S14 has not been selected. The main signal pair may not be used in the absence of a number of receivers (not shown) of the image-processing unit BV of the MRT. The supplementary signal pair S13 and S14 corresponds to the signal from the outputs out2 and out4 and, hence, to the signal from the inputs in2 and in4. The supplementary signal pair S13 and S14 is then transmitted to the MRT image processing BV via the lower transmission channel 4 in FIG. 4.

Thus, a scaling unit 1 is provided that may be used universally for local coils LS with minimum complexity.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description. It is also pointed out that the use of the indefinite article "a" or "an" does not prevent the relevant features from being existent in multiple too.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The invention claimed is:

1. A scaling unit for reception antennae of local coils of a magnetic resonance imaging scanner, the scaling unit comprising:
   a plurality of signal inputs configured for receiving signals from the reception antennae; and
   a plurality of signal outputs configured for outputting unaltered signals, altered signals, or unaltered and altered signals from the reception antennae;
   wherein, at least in a summed signal mode:
      the plurality of signal inputs is connected, for signaling purposes, to a single common signal output of the plurality of signal outputs, such that a sum of signals from the plurality of signal inputs is applied to the single common signal output; and
      each additional signal output of the plurality of signal outputs is connected, for signaling purposes, to a respective single signal input of the plurality of signal inputs, such that an unaltered signal from the respective single signal input is applied to the additional signal output.

2. The scaling unit of claim 1, further comprising:
a switching element configured for changing over, for signaling purposes, the single common signal output to which the sum of signals from the plurality of signal inputs is applied in the summed signal mode to a signal input associated with the single common signal output in a single signal mode;
wherein each signal input of the plurality of signal inputs is connected, for signaling purposes, to a single associated signal output, such that a respective unaltered, signal from the associated signal input of the plurality of signal inputs is applied to the single associated signal output.

3. The scaling unit of claim 1, wherein:
each signal input of the plurality of signal inputs is connected, for signaling purposes, to a single associated signal output of the plurality of signal outputs, such that a respective unaltered signal from an associated signal input is applied to the single associated signal output, wherein an image processing unit of the magnetic resonance imaging scanner is configured to retrieve signals in a single signal mode; and
the plurality of signal inputs, the plurality of signal outputs, or the plurality of signal inputs and the plurality of signal outputs are connected, for signaling purposes, to an additional common signal output, such that a sum of unaltered signals from the plurality of signal inputs is applied to the additional common signal output, wherein the image processing unit of the magnetic resonance imaging scanner is configured to retrieve signals in a summed signal mode.

4. The scaling unit of claim 2, wherein:
each signal input of the plurality of signal inputs is connected, for signaling purposes, to a single associated signal output of the plurality of signal outputs, such that a respective unaltered signal from an associated signal input is applied to the single associated signal output, wherein an image processing unit of the magnetic resonance imaging scanner is configured to retrieve signals in a single signal mode; and
the plurality of signal inputs, the plurality of signal outputs, or the plurality of signal inputs and the plurality of signal outputs are connected, for signaling purposes, to an additional common signal output, such that a sum of unaltered signals from the plurality of signal inputs is applied to the additional common signal output, wherein the image processing unit of the magnetic resonance imaging scanner is configured to retrieve signals in a summed signal mode.

5. A reception device comprising:
a scaling unit for reception antennae of local coils of a magnetic resonance imaging scanner, the scaling unit comprising:
a plurality of signal inputs configured for receiving signals from the reception antennae; and
a plurality of signal outputs configured for outputting unaltered signals, altered signals, or unaltered and altered signals from the reception antennae;
wherein, at least in a summed signal mode:
the plurality of signal inputs is connected, for signaling purposes, to a single common signal output of the plurality of signal outputs, such that a sum of signals from the plurality of signal inputs is applied to the single common signal output; and
each additional signal output of the plurality of signal outputs is connected, for signaling purposes, to a respective single signal input of the plurality of signal inputs, such that an unaltered signal from the respective single signal input is applied to the additional signal output;
wherein each reception antenna of the reception antennae is individually connected, for signaling purposes, to the plurality of signal inputs of the scaling unit; and
wherein the plurality of signal outputs of the scaling unit is configured to be connected, for signaling purposes, to a plurality of associated signal inputs of an image-processing unit of the magnetic resonance imaging scanner.

6. The reception device of claim 5, wherein the scaling unit further comprises:
a switching element configured for changing over, for signaling purposes, the single common signal output to which the sum of signals from the plurality of signal inputs is applied in the summed signal mode to a signal input associated with the single common signal output in a single signal mode;
wherein each signal input of the plurality of signal inputs is connected, for signaling purposes, to a single associated signal output, such that a respective unaltered, signal from the associated signal input of the plurality of signal inputs is applied to the single associated signal output.

7. The reception device of claim 5, wherein:
each signal input of the plurality of signal inputs is connected, for signaling purposes, to a single associated signal output of the plurality of signal outputs, such that a respective unaltered signal from an associated signal input is applied to the single associated signal output, wherein an image processing unit of the magnetic resonance imaging scanner is configured to retrieve signals in a single signal mode; and
the plurality of signal inputs, the plurality of signal outputs, or the plurality of signal inputs and the plurality of signal outputs are connected, for signaling purposes, to an additional common signal output, such that a sum of unaltered signals from the plurality of signal inputs is applied to the additional common signal output, wherein the image processing unit of the magnetic resonance imaging scanner is configured to retrieve signals in a summed signal mode.

8. A local coil for a reception device, the local coil comprising a plurality of reception antennae and at least one scaling unit for the plurality of reception antennae, the at least one scaling unit comprising:
a plurality of signal inputs configured for receiving signals from the reception antennae; and
a plurality of signal outputs configured for outputting unaltered signals, altered signals, or unaltered and altered signals from the reception antennae;
wherein, at least in a summed signal mode:
the plurality of signal inputs is connected, for signaling purposes, to a single common signal output of the plurality of signal outputs, such that a sum of signals from the plurality of signal inputs is applied to the single common signal output; and
each additional signal output of the plurality of signal outputs is connected, for signaling purposes, to a respective single signal input of the plurality of signal inputs, such that an unaltered signal from the respective single signal input is applied to the additional signal output.

9. The local coil of claim 8, wherein the scaling unit further comprises:

a switching element configured for changing over, for signaling purposes, the single common signal output to which the sum of signals from the plurality of signal inputs is applied in the summed signal mode to a signal input associated with the single common signal output in a single signal mode;

wherein each signal input of the plurality of signal inputs is connected, for signaling purposes, to a single associated signal output, such that a respective unaltered, signal from the associated signal input of the plurality of signal inputs is applied to the single associated signal output.

10. The local coil of claim 8, wherein:

each signal input of the plurality of signal inputs is connected, for signaling purposes, to a single associated signal output of the plurality of signal outputs, such that a respective unaltered signal from an associated signal input is applied to the single associated signal output, wherein an image processing unit of the magnetic resonance imaging scanner is configured to retrieve signals in a single signal mode; and the plurality of signal inputs, the plurality of signal outputs, or the plurality of signal inputs and the plurality of signal outputs are connected, for signaling purposes, to an additional common signal output, such that a sum of unaltered signals from the plurality of signal inputs is applied to the additional common signal output, wherein the image processing unit of the magnetic resonance imaging scanner is configured to retrieve signals in a summed signal mode.

11. A reception-and-transmission device comprising a plurality of scaling units for reception antennae of local coils of a magnetic resonance imaging scanner, each scaling unit of the plurality of scaling units comprising:

a plurality of signal inputs configured for receiving signals from the reception antennae; and a plurality of signal outputs configured for outputting unaltered signals, altered signals, or unaltered and altered signals from the reception antennae;

wherein, at least in a summed signal mode:

the plurality of signal inputs is connected, for signaling purposes, to a single common signal output of the plurality of signal outputs, such that a sum of signals from the plurality of signal inputs is applied to the single common signal output; and each additional signal output of the plurality of signal outputs is connected, for signaling purposes, to a respective single signal input of the plurality of signal inputs, such that an unaltered signal from the respective single signal input is applied to the additional signal output;

wherein respective signal outputs to which sums of signals from the plurality of signal inputs are applied are connected, for signaling purposes, to a multiplexer that is connected via a transmission channel to a demultiplexer; and wherein the demultiplexer is configured to individually supply the sums of signals from the plurality of signal inputs of each scaling unit of the plurality of scaling units to an image-processing unit of the magnetic resonance imaging scanner.

12. The reception-and-transmission device of claim 11, wherein:

signal outputs of each scaling unit of the plurality of scaling units, to which signals from respective signal inputs are applied, are electrically connected to a multiplexer;

wherein the multiplexer is connected via a transmission channel to a demultiplexer; and wherein the demultiplexer is configured to individually supply signals on the signal inputs of each scaling unit to the image-processing unit of the magnetic resonance imaging scanner.

13. The reception-and-transmission device of claim 11, wherein the scaling unit further comprises:

a switching element configured for changing over, for signaling purposes, the single common signal output to which the sum of signals from the plurality of signal inputs is applied in the summed signal mode to a signal input associated with the single common signal output in a single signal mode;

wherein each signal input of the plurality of signal inputs is connected, for signaling purposes, to a single associated signal output, such that a respective unaltered, signal from the associated signal input of the plurality of signal inputs is applied to the single associated signal output.

14. The reception-and-transmission device of claim 11, wherein:

each signal input of the plurality of signal inputs is connected, for signaling purposes, to a single associated signal output of the plurality of signal outputs, such that a respective unaltered signal from an associated signal input is applied to the single associated signal output, wherein an image processing unit of the magnetic resonance imaging scanner is configured to retrieve signals in a single signal mode; and the plurality of signal inputs, the plurality of signal outputs, or the plurality of signal inputs and the plurality of signal outputs are connected, for signaling purposes, to an additional common signal output, such that a sum of unaltered signals from the plurality of signal inputs is applied to the additional common signal output, wherein the image processing unit of the magnetic resonance imaging scanner is configured to retrieve signals in a summed signal mode.

15. The reception-and-transmission device of claim 12, wherein the scaling unit further comprises:

a switching element configured for changing over, for signaling purposes, the single common signal output to which the sum of signals from the plurality of signal inputs is applied in the summed signal mode to a signal input associated with the single common signal output in a single signal mode;

wherein each signal input of the plurality of signal inputs is connected, for signaling purposes, to a single associated signal output, such that a respective unaltered, signal from the associated signal input of the plurality of signal inputs is applied to the single associated signal output.

16. The reception-and-transmission device of claim 12, wherein:

each signal input of the plurality of signal inputs is connected, for signaling purposes, to a single associated signal output of the plurality of signal outputs, such that a respective unaltered signal from an associated signal input is applied to the single associated signal output, wherein an image processing unit of the magnetic resonance imaging scanner is configured to retrieve signals in a single signal mode; and the plurality of signal inputs, the plurality of signal outputs, or the plurality of signal inputs and the plurality of signal outputs are connected, for signaling purposes, to an additional common signal output, such that a sum of unaltered signals from the plurality of signal inputs is applied to the additional common signal output, wherein the image processing unit of the magnetic resonance imaging scanner is configured to retrieve signals in a summed signal mode.

17. A magnetic resonance imaging scanner comprising a reception-and-transmission device and a scaling unit for reception antennae of local coils of the magnetic resonance imaging scanner, the scaling unit comprising:
- a plurality of signal inputs configured for receiving signals from the reception antennae; and
- a plurality of signal outputs configured for outputting unaltered signals, altered signals, or unaltered and altered signals from the reception antennae;
- wherein, at least in a summed signal mode:
  - the plurality of signal inputs is connected, for signaling purposes, to a single common signal output of the plurality of signal outputs, such that a sum of signals from the plurality of signal inputs is applied to the single common signal output; and
  - each additional signal output of the plurality of signal outputs is connected, for signaling purposes, to a respective single signal input of the plurality of signal inputs, such that an unaltered signal from the respective single signal input is applied to the additional signal output.

18. The magnetic resonance imaging scanner of claim 17, wherein signal outputs of the scaling unit to which signals from respective signal inputs are applied are electrically connected to a multiplexer;
- wherein the multiplexer is connected via a transmission channel to a demultiplexer; and
- wherein the demultiplexer is configured to individually supply signals on the signal inputs of each scaling unit to an image-processing unit of the magnetic resonance imaging scanner.

19. A method for signal transmission comprising:
using a scaling unit for reception antennae of local coils of a magnetic resonance imaging scanner, a reception device comprising the scaling unit, a local coil for the reception device, a reception-and-transmission device comprising the scaling unit, or a magnetic resonance imaging scanner comprising the reception-and-transmission device;
wherein the scaling unit comprises:
- a plurality of signal inputs configured for receiving signals from the reception antennae; and
- a plurality of signal outputs configured for outputting unaltered signals, altered signals, or unaltered and altered signals from the reception antennae;
- wherein, at least in a summed signal mode:
  - the plurality of signal inputs is connected, for signaling purposes, to a single common signal output of the plurality of signal outputs, such that a sum of signals from the plurality of signal inputs is applied to the single common signal output; and
  - each additional signal output of the plurality of signal outputs is connected, for signaling purposes, to a respective single signal input of the plurality of signal inputs, such that an unaltered signal from the respective single signal input is applied to the additional signal output.

20. The method of claim 19, further comprising:
calculating a value of a signal from a reception antenna at a signal input that is not directly connected to an associated signal output in the summed signal mode;
wherein the calculating is based on the sum of signals from the plurality of signal inputs that is applied to the associated signal output minus a sum of remaining single signals that are applied to remaining signal inputs or signal outputs.

* * * * *